US00PP14140P29

(12) United States Plant Patent
Dittmar

(10) Patent No.: US PP14,140 P2
(45) Date of Patent: Sep. 16, 2003

(54) SANVITALIA PLANT NAMED 'DITTSUN'

(76) Inventor: Hugo Dittmar, Schaffnaustr. 9, CH-4543 Deitingen (CH)

( * ) Notice: Subject to any disclaimer, the term of this patent is extended or adjusted under 35 U.S.C. 154(b) by 0 days.

(21) Appl. No.: 10/142,847

(22) Filed: May 10, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A new and distinct cultivar of Sanvitalia plant named 'Dittsun', characterized by its compact, low mounded and outwardly spreading plant habit; freely branching habit and short internodes, dense and bushy plants; dark green foliage; freely flowering habit with flowers held just above and beyond the foliage; and single daisy inflorescence form with yellow-colored ray florets.

1 Drawing Sheet

Botanical classification/cultivar denomination: *Sanvitalia speciosa* cultivar Dittsun.

BACKGROUND OF THE INVENTION

The present invention relates to a new and distinct cultivar of Sanvitalia plant, botanically known as *Sanvitalia speciosa* and hereinafter referred to by the cultivar name 'Dittsun'.

The new Sanvitalia is a product of a planned breeding program conducted by the Inventor in Deitingen, Switzerland. The objective of the program is to create and develop new compact Sanvitalia cultivars with numerous inflorescences and attractive ray floret coloration.

The new Sanvitalia originated from a self-pollination by the Inventor of the *Sanvitalia speciosa* cultivar Aztekengold, not patented. The new Sanvitalia was discovered and selected by the Inventor as a plant within the progeny of the stated self-pollination in a controlled environment in Deitingen, Switzerland in 1997. The selection of the new Sanvitalia was based on its compact and freely flowering habit.

Asexual reproduction of the new Sanvitalia by terminal cuttings taken in a controlled environment in Deitingen, Switzerland since 1997, has shown that the unique features of this new Sanvitalia are stable and reproduced true to type in successive generations.

SUMMARY OF THE INVENTION

The new Sanvitalia has not been observed under all possible environmental conditions. The phenotype may vary somewhat with variations in environment such as temperature and light intensity without, however, any variance in genotype.

The following characteristics have been repeatedly observed and are determined to be basic characteristics of 'Dittsun' and distinguish the new Sanvitalia as a new and distinct cultivar:

1. Compact, low mounded and outwardly spreading plant habit.
2. Freely branching habit and short internodes, dense and bushy plants.
3. Dark green foliage.

4. Freely flowering habit with flowers held just above and beyond the foliage.
5. Single daisy inflorescence form with yellow-colored ray florets.

Plants of the new Sanvitalia are most similar to plants of the parent, the cultivar Aztekengold. In side-by-side comparisons conducted in Deitingen, Switzerland, plants of the new Sanvitalia differed from plants of the cultivar Aztekengold in the following characteristics:

1. Plants of the new Sanvitalia were more compact than plants of the cultivar Aztekengold.
2. Plants of the new Sanvitalia had shorter internodes than plants of the cultivar Aztekengold.
3. Plants of the new Sanvitalia had tighter inflorescences (less open form) than plants of the cultivar Aztekengold.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Sanvitalia.

The photograph at the top of the sheet comprises a side perspective view of three typical flowering plants of 'Dittsun' grown in a 20-cm container.

The photograph at the bottom of the sheet comprises a close-up view of typical leaves, an inflorescence bud, a developing inflorescence, and fully opened inflorescences of 'Dittsun'.

DETAILED BOTANICAL DESCRIPTION

The aforementioned photographs, following observations and averaged measurements describe plants grown in Bonsall, Calif., in an outdoor nursery under full sunlight during the spring with day temperatures ranging from 18 to 35° C. and night temperatures ranging from 7 to 18° C. Plants were grown for about 12 weeks in 20-cm containers with three plants per container. Plants were pinched one time. Color references are made to The Royal Horticultural Society Colour Chart, 1995 Edition, except where general terms of ordinary dictionary significance are used.

Botanical classification: *Sanvitalia speciosa* cultivar Dittsun.

Parentage: Self-pollination of *Sanvitalia speciosa* cultivar Aztekengold, not patented.

Propagation:

*Type.*—Terminal vegetative cuttings.

*Time to initiate roots.*—Summer: About 14 days at 20 to 22° C. Winter: About 18 days at 20 to 22° C.

*Time to produce a rooted cutting.*—Summer: About 21 days at 18 to 20° C. Winter: About 25 days at 18 to 20° C.

*Root description.*—Fine; white in color.

Plant description:

*General appearance.*—Compact, low mounded, and outwardly spreading plant form with dense foliage and inflorescences held just above and beyond the foliage. Moderately vigorous growth habit.

*Plant height.*—About 18 cm.

*Plant width, per plant.*—About 26 cm.

*Lateral branch description.*—Quantity per plant: Freely branching, about 14 lateral branches. Length: About 30 cm. Diameter: About 3 mm. Internode length: About 3 cm. Aspect: Outwardly spreading. Texture: Slightly pubescent. Color: 144D overlain with close to 187A.

*Foliage description.*—Arrangement: Opposite, simple; sessile. Length: About 2.2 cm. Width: About 7 mm. Shape: Elliptic. Apex: Acute. Base: Clasping. Margin: Entire; deeply and finely incised. Texture, upper surface: Slightly coarse; towards apex, pubescent. Texture, lower surface: Smooth, glabrous. Venation pattern: Pinnate. Color: Young and fully expanded foliage, upper surface: 147A. Young and fully expanded foliage, lower surface: 147B. Venation, upper surface: 144D. Venation, lower surface: 147B.

Inflorescence description:

*Appearance.*—Single daisy composite inflorescence form with ligulate ray florets. Disc and ray florets arranged acropetally on a capitulum. Inflorescences held upright on terminal and axillary peduncles. Inflorescences upright to outward and perpendicular to the peduncles. Inflorescences persistent. Inflorescences not fragrant.

*Flowering response.*—Under natural conditions, plant flower continuously from April to October.

*Inflorescence longevity.*—Inflorescences last about seven to ten days on the plant.

*Quantity of inflorescences.*—Freely flowering, about 18 buds and inflorescences per lateral branch.

*Inflorescence size.*—Diameter: About 1.3 cm. Depth (height): About 5 mm. Diameter of disc: About 6 mm.

*Inflorescence buds, at stage of showing color.*—Height: About 4 mm. Diameter: About 7 mm. Shape: Oblate. Color: 144C.

*Ray florets.*—Quantity per inflorescence: About 13 arranged in a single whorl. Shape: Ligulate. Length: About 5 mm. Width: About 2 mm. Apex: Slightly emarginate. Base: Acute. Margin: Entire. Texture, upper and lower surfaces: Smooth, glabrous. Aspect: Initially upright and cupped; when mature, about 90° from vertical. Color: When opening and fully opened, upper surface: 14B. When opening and fully opened, lower surface: 14C with longitudinally streaks, 144C.

*Disc florets.*—Arrangement: Massed at the center of the inflorescence. Quantity per inflorescence: About 100. Shape: Tubular, five-parted at apex; apex, acute; base, fused. Length: About 2 mm. Diameter, apex: About 1 mm. Diameter, base: Less than 1 mm. Color: Immature: 144B. Mature, apex and mid-section: 145C. Mature, base: 145D.

*Involucral bracts* (*phyllaries*).—Quantity per inflorescence: About five. Length: About 4 mm. Width: About 4 mm. Shape: Elliptic. Apex: Acute. Base: Truncate. Margin: Entire. Texture, upper and lower surfaces: Glabrous, slightly rough. Color: Upper surface: 146C. Lower surface: 146B.

*Peduncle.*—Strength: Strong. Aspect: Upright to about 30° from vertical. Length: About 1 cm. Diameter: About 1.5 mm. Texture: Slightly pubescent. Color: 146B overlain with close to 187A.

*Reproductive organs.*—Androecium: Present on disc florets only. Quantity per floret: Five. Anther shape: Oblong. Anther length: Less than 1 mm. Anther color: 22B. Amount of pollen: Scarce. Pollen color: 22B. Gynoecium: Quantity per floret: One. Pistil length: About 2 mm. Stigma shape: Two-parted. Stigma color: 145A. Style length: About 1 mm. Style color: 145A. Ovary color: 145D. Seed/fruit: Seed and fruit production has not been observed.

Disease/pest resistance: Resistance to pathogens and pests common to Sanvitalias has not been observed on plants grown under commercial conditions.

Temperature/weather tolerance: Plants of the new Sanvitalia have been observed to be tolerant to rain, wind and to temperatures from 2 to 35° C.

It is claimed:

1. A new and distinct cultivar of Sanvitalia plant named 'Dittsun', as illustrated and described.

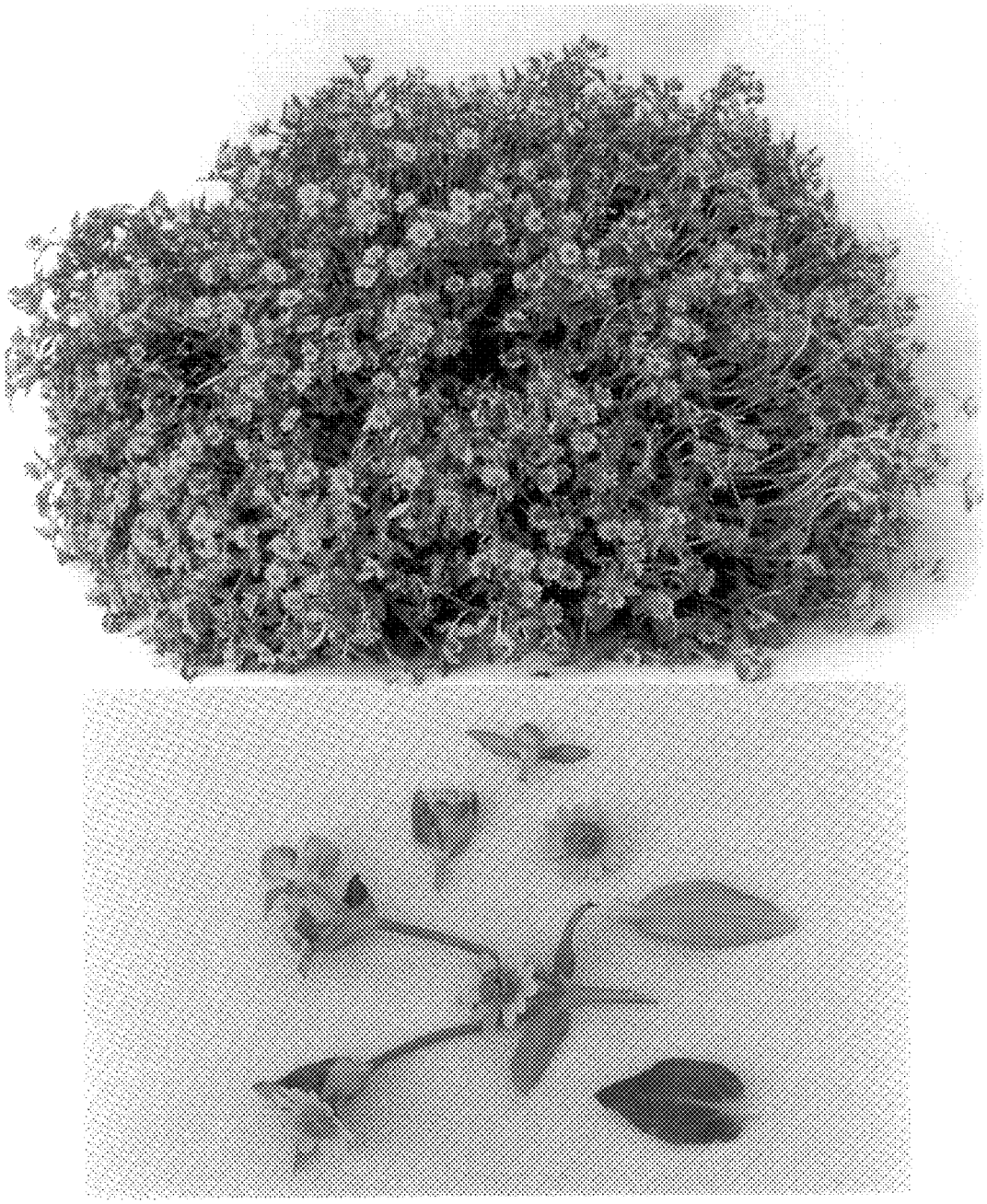

* * * * *